(12) United States Patent
DiGregorio et al.

(10) Patent No.: US 8,241,544 B2
(45) Date of Patent: Aug. 14, 2012

(54) SYRINGES AND METHODS OF SYRINGE MANUFACTURING

(75) Inventors: Henry DiGregorio, Westerly, RI (US); John Higson, North Dighton, MA (US); Jeffery White, Warwick, RI (US)

(73) Assignee: Nordson Corporation, Westlake, OH (US)

( * ) Notice: Subject to any disclaimer, the term of this patent is extended or adjusted under 35 U.S.C. 154(b) by 259 days.

(21) Appl. No.: 12/720,896

(22) Filed: Mar. 10, 2010

(65) Prior Publication Data
US 2010/0163574 A1 Jul. 1, 2010

Related U.S. Application Data

(62) Division of application No. 10/829,126, filed on Apr. 21, 2004, now Pat. No. 7,677,419.

(51) Int. Cl.
*B28B 17/00* (2006.01)

(52) U.S. Cl. ......... 264/162; 264/138; 264/296; 604/187

(58) Field of Classification Search .................. 264/162, 264/138, 296; 604/187, 218
See application file for complete search history.

(56) References Cited

U.S. PATENT DOCUMENTS

| | | | | | |
|---|---|---|---|---|---|
| 3,291,128 | A | * | 12/1966 | O'Neil ........................... | 604/125 |
| 5,009,587 | A | * | 4/1991 | Corvaglia et al. ............. | 425/549 |
| 2002/0023347 | A1 | * | 2/2002 | Hannewald et al. ..... | 29/890.124 |
| 2005/0221035 | A1 | * | 10/2005 | Wyatt ........................... | 428/35.7 |

* cited by examiner

*Primary Examiner* — Christina Johnson
*Assistant Examiner* — Galen Hauth
(74) *Attorney, Agent, or Firm* — Wood, Herron & Evans, LLP

(57) ABSTRACT

A syringe for holding fluids susceptible to void formation when frozen and thawed before use. The interior surface of the syringe sidewall may be roughened, which serves to prevent or significantly reduce the incidence of void formation in the fluid. The required level of surface roughening for counteracting void formation may be reduced by increasing the sidewall flexibility. Alternatively, the flexibility of the syringe sidewall may operate over certain thickness ranges to prevent or significantly reduce void formation in the fluid without intentionally roughening the interior surface.

8 Claims, 5 Drawing Sheets

SYRINGES AND METHODS OF SYRINGE MANUFACTURING

CROSS REFERENCE TO RELATED APPLICATION

This application is a divisional of application Ser. No. 10/829,126, filed Apr. 21, 2004, the disclosure of which is hereby incorporated by reference herein in its entirety.

FIELD OF THE INVENTION

This invention relates generally to syringes and, more particularly, to syringes for dispensing fluids that are frozen for storage and then thawed from the frozen state shortly before use.

BACKGROUND OF THE INVENTION

Syringes containing a frozen fluid, such as premixed curable liquids, epoxies, pastes, thixotropic liquids, and adhesives, are used in applications including, but not limited to, semiconductor and optoelectronic packaging. The syringe, also referred to by conventional terms such as cartridge, barrel, tube, or reservoir, dispenses the frozen fluid after it is thawed. Premixing adhesives and pastes eliminates handling and weighing individual components, the mess associated with mixing these components, testing before and after mixing for quality assurance, training employees to handle hazardous raw materials, and the need to dispose of hazardous wastes. The syringe is filled with fluid at room temperature, frozen at temperature below the fluid's freezing point, and shipped in a thermally insulated container from the manufacturer at a temperature of about −40° C. to about −80° C. (i.e., on dry ice). The end user stores the frozen syringe and fluid in a low-temperature freezer at a temperature less than the fluid's freezing point. Low temperature storage extends the working life, delays aging and prevents curing, which thereby extends or prolongs the shelf life of the fluid. The end user warms the syringe and fluid to ambient temperature shortly before dispensing the fluid from the syringe. After the fluid is dispensed, the syringe is discarded.

Syringes containing such frozen fluids are susceptible to a phenomenon known as freeze-thaw voiding when thawed from the frozen state. Specifically, the frozen fluid and the syringe each shrink in dimensions or contract when frozen. Differential shrinkage arises from the different coefficients of thermal expansion of the material forming the syringe and the fluid. During thawing, the sidewall of the syringe warms faster than the frozen mass of fluid held inside the syringe. Because the syringe sidewall and the frozen mass of fluid do not thaw simultaneously, the sidewall expands first and pulls away from the frozen fluid. This separation creates an air-filled space between the frozen mass of fluid and the sidewall. As the fluid thaws and re-wets arbitrary regions of the syringe sidewall, air bubbles or pockets are surrounded by the regions of fluid and subsequently trapped between the fluid and sidewall. The trapped air pockets, termed by some as freeze-thaw voids, have an adverse impact on the dispensability of the fluid. Dispensing fluid laced with air-filled voids causes dispensing inconsistencies, such as tailing, dripping, dispense voids, and weight variations.

For some fluids, freeze-thaw voids are observed to form in the vast majority of fluid-filled syringes. Depending upon the type of fluid, the voids may self-alleviate by migrating to the vicinity of the syringe plunger and may be passed rearwardly past the periphery of the plunger. For other fluids, the voids have fixed locations and are not self-alleviating. Then, either the entire syringe is discarded without use to avoid the potential for dispensing the voids or the fluid is carefully dispensed from the syringe without dispensing the voids. In this latter circumstance, only a portion of the fluid is dispensed and the syringe is ultimately discarded with unused fluid remaining inside the syringe.

It would therefore be desirable to provide a syringe for fluids that reduces or minimizes the incidence of freeze-thaw voiding.

SUMMARY OF THE INVENTION

In accordance with one embodiment of the invention, a syringe includes a barrel with a sidewall having an inwardly-facing surface. A portion of the sidewall forms a reservoir to contain a fluid, such as a curable paste or an adhesive, susceptible to void formation when frozen and thawed before dispensing. The inwardly-facing surface of the sidewall portion forming the reservoir is roughened with a surface roughness effective to significantly reduce void formation in the thawed fluid.

In yet another embodiment of the invention, a method is provided for manufacturing a syringe to dispense a fluid susceptible to void formation when frozen and thawed before dispensing. The method includes forming the syringe about a core inside a mold such that a sidewall of the syringe forms about the core with an inwardly-facing surface in contact with the core. The method further includes separating the syringe from the core such that ribs on the core form lengthwise grooves in the inwardly-facing surface, in which the grooves are configured to significantly reduce void formation between the inwardly-facing surface and the fluid when the fluid is frozen and thawed.

The syringes of the invention eliminate or significantly reduce void formation because roughening the interior surface of the syringe sidewall increases the adhesion between the frozen fluid and the interior surface when the temperature is elevated to thaw the frozen fluid. As a result, the yield of usable syringes that do not experience dispensability problems as a consequence of freeze/thaw voids is increased because separation or delamination of the sidewall from the frozen fluid is eliminated or, at the least, is significantly reduced. The level of surface roughness required to eliminate or, at the least, significantly reduce void formation may be reduced as the syringe sidewall flexibility is increased. Sidewall flexibility will depend upon the material forming the sidewall and the sidewall thickness, among other variables.

In yet another embodiment, a method includes filling a barrel of a syringe with a fluid such that an inwardly-facing surface of a sidewall of the barrel and a plurality of axial grooves with parallel alignment on the inwardly facing surface are contacted by the fluid. The method further includes disposing a piston inside the sidewall of the barrel to define a fluid chamber between the piston and a first opening in the sidewall that is in fluid communication with the fluid chamber and to provide a fluid seal with the axial grooves to inhibit fluid leakage from the fluid chamber between the piston and the inwardly-facing surface. The syringe and fluid are then frozen.

By eliminating or significantly reducing void formation in this manner, the dispensability of the fluid is improved. The syringe of the invention may be used without special handling by the end user and then discarded after use. By eliminating or significantly reducing air pockets trapped inside the syringe, fewer syringes must be discarded and/or the risk of a void degrading dispensability is eliminated or significantly reduced.

Various objects, advantages and advantages of the invention shall be made apparent from the accompanying drawings of the illustrative embodiment and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE PREFERRED EMBODIMENTS

Figure 1:
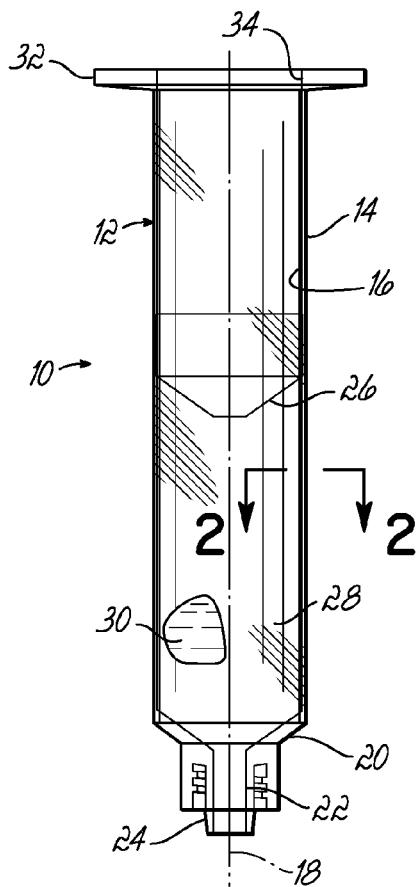
FIG. 1 is a side view of a syringe filled with fluid.
Figure 2:
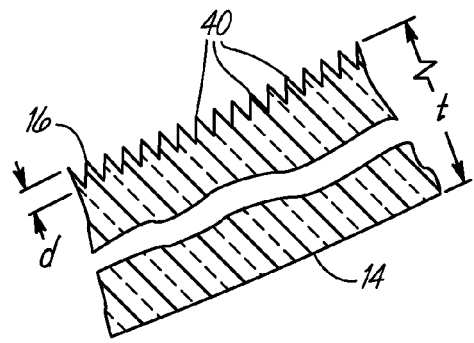
FIG. 2 is an enlarged view taken generally along line 2-2 of a portion of the interior surface of the barrel of the syringe of FIG. 1.

With reference to FIGS. 1 and 2, a syringe 10 generally includes a barrel 12 having a substantially-cylindrical sidewall 14 with an inwardly-facing interior surface 16 centered along a longitudinal axis 18. A tapered frustoconical region 20 of the sidewall 14 converges to a stepped-diameter fluid outlet 22 located inside a nozzle 24, which is depicted as a luer taper orifice. The nozzle 24 is adapted to mate with the hub of a suitable dispensing tip (not shown). Provided inside of the barrel 12 is a wiper or piston 26 that has an interference fit with the sidewall 14 to define a reservoir 28, which is occupied when filled by a volume of a fluid 30, such as a curable liquid, a paste or an adhesive. The reservoir 28 is surrounded by the sidewall 14 and the fluid 30 held in the reservoir 28 wets the forward end of the piston 26 as well as the interior surface 16. Although the maximum volumetric capacity of the reservoir 28 may vary, typical capacities range from one (1) cc to seventy-five (75) cc. Ears or flanges 32a,b are disposed at the rearward end of the barrel 12 opposite to the fluid outlet 22. The syringe nozzle 24 and a complementarily tapered receptacle in the hub of the tip may be standard Luer fittings. Common construction materials for the syringe 10 are polymers including, but not limited to, polypropylene and polyethylene, as well as blends and copolymers of these and other polymers.

The non-wetted rear end of the piston 26 is accessible through a rearward opening 34. Opening 34 has substantially the same cross-section profile as the barrel 12, making the opening 34 substantially a continuation, or ending, of the barrel 12 and suitably the opening edge roughly corresponds to a cross-section of the barrel 12 perpendicular to the longitudinal axis 18. The periphery of the piston 26 provides a fluid seal with the interior surface 16 so that, when the piston 26 is advanced to drive fluid 30 in the reservoir 28 toward the fluid outlet 22, little if any fluid 30 leaks rearwardly past the piston 26 toward opening 34. The interference fit of the piston 26 with the interior surface 16 may be adjusted such that any pressure transferred from the piston 26 to the fluid 30 is quickly released when a force that is advancing piston 26 toward fluid outlet 22 is removed or discontinued.

With continued reference to FIGS. 1 and 2, the interior surface 16 of the barrel 12 includes a plurality of features 40 that operate to increase the contact area of surface 16 over which surface 16 is wetted by the fluid 30. In the preferred embodiment, the features 40 have the form of serrations or grooves. Portions of fluid 30 inside reservoir 28 fill the features 40. The increase in the contact area increases the adhesive forces acting between the frozen fluid 30 and the interior surface 16 during thawing. The increase in contact area is achieved by roughening interior surface 16 with an average surface roughness that exceeds the average surface roughness of a conventional syringe used for holding such fluids 30. The average surface roughness of a typical conventional syringe is believed to be about 0.1 microns, which represents an unroughened syringe surface. The surface roughness may be determined as the arithmetical mean deviation of the vertical height of the surface features or $R_a$. The surface roughness of interior surface 16 may be measured by various techniques, including but not limited to surface profilometry. Features 40 supply a level of surface roughness effective to prevent or, at the least, significantly reduce void formation in fluid 30.

The features 40 are depicted in FIG. 2 as pointed or "V" shaped grooves, although the invention is not so limited. In various alternative embodiments, the grooved features 40 may be of any of a number of shapes, or of a variety of shapes and sizes, including, but not limited to, cross-sectional profiles viewed from a perspective parallel to longitudinal axis 18 that are double sloped (two gradients on the same groove), rounded "U", squared "U", hemispherical, elongated, rounded "V" shaped, crescent or "C" shaped, "I" shaped, or the like. Without wishing to be bound by theory, it is believed that cross-sectional profiles characterized by sharp edges may enhance the adhesive forces acting between the frozen fluid 30 and grooved features 40. All suitable geometric shapes or angles are contemplated as being within the scope of the present invention, such as a network of crossing and/or interconnected features 40.

Features 40, as represented by grooves, may extend the full length and circumference of the wetted portion of the interior surface 16 between piston 26 and fluid outlet 22 or, alternatively, may be present over less than the entire interior surface 16. For example, the features 40 may be confined to discontinuous bands along the length of the surface 16 or, alternatively, may extend the full length of surface 16 but be confined to angular arcs spaced about the circumference of surface 16. Features 40 have an average depth or draft, d, measured radially as the average linear distance between the point of each feature 40 most distant from longitudinal axis 18 and the point of each corresponding feature 40 closest to axis 18.

Features 40 may be of different shapes, such as random or rows of shaped features 40 or even a gradient of sized features 40. The features 40 may be have any orientation including but not limited to circumferential, helical, and longitudinal. In illustrated embodiment, the features 40 are aligned parallel to the longitudinal axis 18 of the syringe 10 so as to be lengthwise non-intersecting and the parallel features 40 have spaced uniformly about the circumference of the sidewall 14.

With renewed reference to FIGS. 1 and 2, the level of surface roughness contributed by features 40 in maintaining contact between sidewall 14 and the frozen mass of fluid 30 during thawing is believed to depend upon, among other variables, the characteristics (e.g., viscosity, rheology, etc.) of the fluid 30 filling reservoir 28 and the flexibility of the sidewall 14. The flexibility of the sidewall 14 is dependent upon, among other factors, the thickness, t, as measured between the interior surface 16 and the outer sidewall surface, the constituent material, and the level of surface roughness introduced by features 40. Without wishing to be limited by theory, increasing the flexibility of sidewall 14 is believed to lessen the roughening level (i.e., average surface roughness) of the sidewall 14 effective for eliminating or significantly reducing void formation and thereby improves the yield of usable syringes 10. If the sidewall is formed from polypropylene, the minimum sidewall thickness at which the sidewall 14 will resist rupture is believed to be about 15 mils for typical maximum fluid pressures of about 50 pounds per square inch (psi) observed during dispensing.

Figure 3:
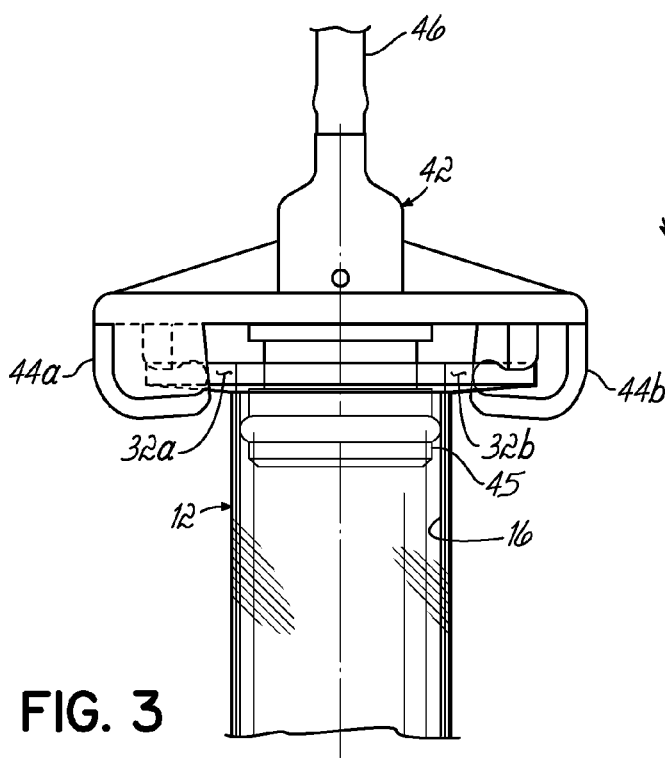
FIG. 3 is a side view of the syringe of FIG. 1 having an adapter effective for pneumatically coupling the syringe with a timer controller.

In use and with continued reference to FIGS. 1-3, the reservoir 28 of syringe 10 is filled, typically at room or ambient temperature, with a volume of the fluid 30 either by introducing fluid 30 through rearward opening 34 and then inserting the piston 26 or by aspirating fluid 30 into reservoir 28 through the fluid outlet 22 by rearward movement of piston 26. Portions of the fluid 30 fill the features 40 and wet the individual inclined sidewalls of features 40. The syringe 10 is placed in a refrigerated environment at a temperature below the freezing point of the fluid 30 and is stored indefinitely at a temperature suitable to extend the working life. For typical fluids 30, the syringe 10 is frozen and stored at temperatures in the range of about −40° C. to about −80° C., although the invention is not so limited.

The sidewall 14 and the fluid 30 shrink by different amounts when the fluid 30 is frozen to its freezing point or below due to differences in coefficients of thermal expansion. Shortly before use, the syringe 10 is removed from the refrigerated environment and warmed to ambient temperature with the intention of thawing the frozen fluid 30. For example, the syringe 10 may be placed on a bench top for a time sufficient to warm the fluid 30 to ambient temperature. The area of interior surface 16 that is in contact with the frozen fluid 30 is increased by the increased surface roughness originating from features 40. The increased contact area promotes increased adhesion between the interior surface 16 and the frozen mass of fluid 30 as the sidewall 14 thaws. As a result, the sidewall 14, which thaws first, does not pull away (i.e., delaminate, detach or separate) or, at the least, is significantly less likely to pull away from the frozen mass of fluid 30. Instead, the frozen fluid 30 remains attached to interior surface 16 as the sidewall 14 thaws. As the frozen fluid 30 thaws, the interior surface 16 is wetted by the thawed fluid 30 without entrapment of air in bubbles or voids. Hence, syringe 10 prevents or, at the least, significantly reduces void formation and thereby improves the yield of usable syringes 10.

With specific reference to FIG. 3, the thawed fluid 30 is dispensed from the syringe 10 onto a product, such as a semiconductor package or an optoelectronic package. To that end, the syringe 10 is coupled by an adapter 42 with an air powered dispenser (not shown) typically including a microprocessor-based timer/controller. The adapter 42 has arms 44a, 44b is mechanically coupled with the flanges 32a,b and has a plug 45 inserted into the rearward opening 34. Plug 45 has a sealed engagement with the interior surface 16. Air pressure is supplied from the timer/controller through a passageway partially in a conduit 46 and extending through the plug 45 to the space inside barrel 12 between the adapter 42 and the piston 26. Pressurizing this space with a sufficient air pressure overcomes the hydraulic resistance presented by the fluid 30 and the stiction of the piston 26 for advancing piston 26 toward the outlet 22. As the piston 26 advances, amounts of the fluid 30 are driven forward toward and out of the outlet 22. The pressurization of the headspace between piston 26 and plug 45 may be pulsed during dispensing.

The syringe 10 may be used for dispensing any fluid 30, such as a liquid, that has flow properties and that is susceptible to void formation when frozen and thawed before use or dispensing. Included among this class of fluids 30 are premixed curable liquids, epoxies, pastes, thixotropic (shear thinning) liquids, adhesives, and liquids having a viscosity ranging from 1 centipoise (cps) to 1,000,000 cps. Exemplary liquids that are suitable for storing frozen in syringe 10 and that are susceptible to void formation when frozen and thawed include, but are not limited to, curable liquids, pastes and adhesives for example semiconductor, microelectronics and optoelectronics packaging applications commercially available from Ablestik Laboratories (Rancho Dominguez, Calif.), Dymax Corporation (Torrington, Conn.), and Henkel Loctite Corporation (Dusseldorf, Germany).

Figure 2A:
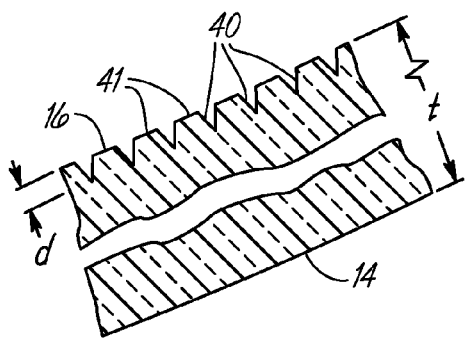
FIG. 2A is a view similar to FIG. 2 in accordance with an alternative embodiment of the invention.
Figure 6:
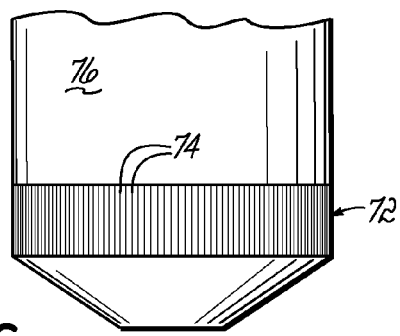
FIG. 6 is an enlarged view of a portion of the core of FIG. 5.

With reference to FIG. 2A in which like reference numerals refer to like features in FIG. 2 and in accordance with an alternative embodiment of the invention, each of the features 40 may be recessed or depressed with respect to radial lands or margins 41 defined between adjacent features 40. Each land 41 represents a portion of the barrel surface 16 having a constant radius measured relative to the longitudinal axis 18. The invention contemplates the lands 41 may result from elastic recovery of the material of interior surface 16 after scoring by ribs 74 (FIG. 6). Alternatively, the ribs 74 may only penetrate a limited distance into the material of the interior surface 16. Features 40 supply a level of surface roughness effective to prevent or, at the least, significantly reduce void formation in fluid 30 and thereby improves the yield of usable syringes 10.

Figure 2B:
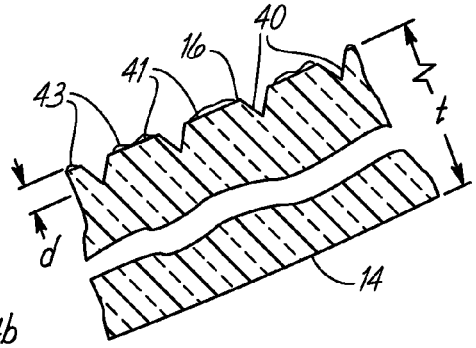
FIG. 2B is a view similar to FIGS. 2 and 2B in accordance with an alternative embodiment of the invention.

With reference to FIG. 2B in which like reference numerals refer to like features in FIG. 2A and in accordance with an alternative embodiment of the invention, the interior surface 16 may further include features 43 on lands 41 represented by irregularities, indentations, projections, dimples, protuberances, or any other abrupt changes in surface geometry, in conjunction with features 40. Features 43 increase the surface roughness and the contact area with the fluid 30 in reservoir 28 (FIG. 1) by defining recessed locations capable of being wetted or filled by amounts of fluid 30. The increased surface or contact area of wetting operates to increase the adhesive force acting between the frozen mass of fluid 30 and the interior surface 16. Features 40 and 43 supply a level of surface roughness effective to prevent or, at the least, significantly reduce void formation in fluid 30 and thereby improves the yield of usable syringes 10. The invention contemplates that features 43 may also be superimposed on the inclined walls of features 40 in yet another alternative embodiment. In yet another alternative embodiment of the invention, features 40 may be omitted such that features 43 provide the only contribution to the surface roughness of the interior surface 16.

In accordance with an exemplary embodiment of the invention, the sidewall 14 of syringe 10 may be composed of polypropylene and have a thickness in the range of about 0.019" to about 0.025". The interior surface 16 may have a surface roughness ($R_a$) in the range of about 2.5 μm to about 5.1 μm, in which features 43 make a contribution of about 1.4 μm to about 1.8 μm to the total surface roughness and features 40 make the remaining contribution to the total surface roughness.

Figure 4:
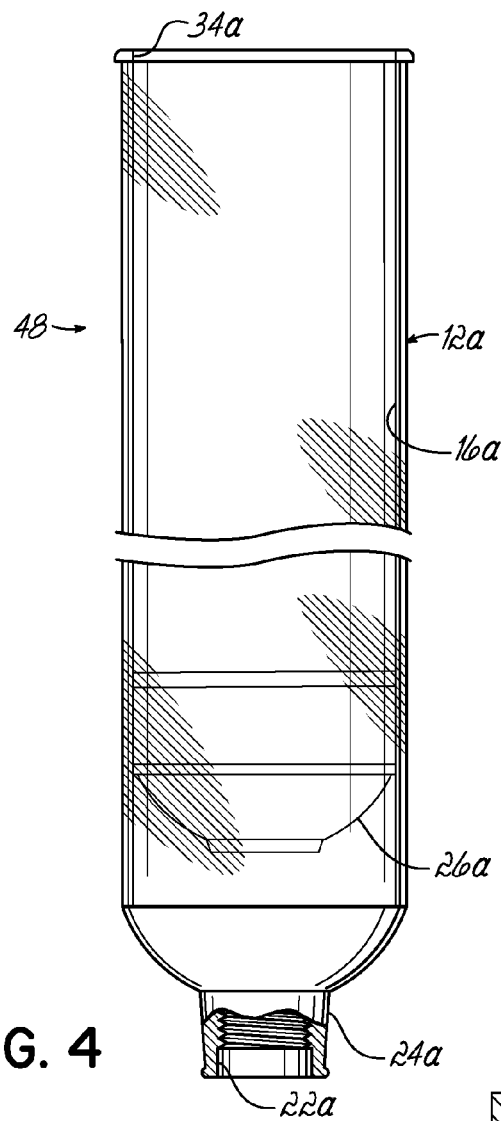
FIG. 4 is a side view of a syringe in accordance with an alternative embodiment of the invention.

With reference to FIG. 4 in which like reference numerals refer to like features in FIGS. 1 and 2 and in accordance with an alternative embodiment, a syringe 48 includes a barrel 12a that lacks ears or flanges proximate to rearward opening 34a but is otherwise similar to syringe 10. Although the maximum volumetric capacity of syringe 48 may vary, typical capacities range from about 2.5 fluid ounces to about 32 fluid ounces. The nozzle 24a, in which a fluid outlet 22a is defined, is adapted to mate with the hub of a suitable tip (not shown). The interior surface 16a of syringe 48 includes surface roughness (not shown) characterized by features 40 and/or features 43 as described above with regard to the interior surface 16 of syringe 10 and as depicted in FIGS. 2, 2A and 2B.

Figure 5:
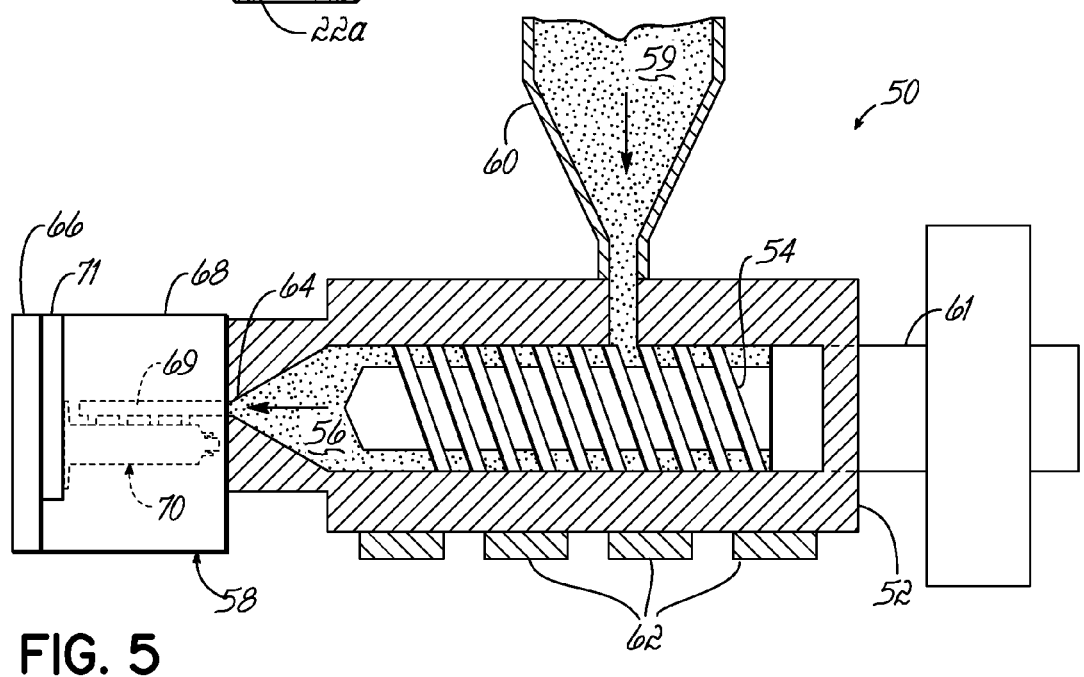
FIG. 5 is a diagrammatic cross-sectional view of an injection molding apparatus suitable for forming the syringe of FIG. 1.

With reference to FIGS. 5 and 6, the features 40 and/or features 43 may be formed in the interior surface 16 of the sidewall 14 by a multitude of different techniques, such as during ejection from an injection molding machine 50. Injection-molding machine 50 includes a heated barrel 52 and a screw 54 used to melt, mix, and pump a molten polymer 56 heated in the barrel 52 into a mold 58. A solid polymer resin 59 in the form of pellets or powder is fed from a hopper 60 into the barrel 52 and melted by heat transferred by conduction from heaters 62 to create the molten polymer. Rotation of the screw 54, along with optional axial reciprocation, mixes and injects the molten polymer 56. Optionally, the injection-molding machine 50 may rely upon a hydraulically operated ram or plunger 61 to inject the molten polymer into the mold 58. The screw-driven molten polymer converges at a nozzle 64 and is injected through a sprue bushing into a network of passageways 69 inside the mold 58. A clamping unit consisting of a moving platen 66 and a fixed platen 68 holds the mold 58 together during polymer injection.

A mold core 70 has a tip region 72 bearing lengthwise ribs 74. The core 70 is a non-consumable component reused in subsequent molding cycles to form successive syringes 10. Molten polymer 56 is supplied from the network of passageways 69 into an open space defined between the mold 58 and the core 70. The shape of the open space resembles the final shape of the syringe 10. The ribs 74 in the tip region 72 extend only along a narrow band of an exterior surface 76 of the core 70 and are circumferentially spaced with a substantially uniform angular spacing. The ribs 74 may be formed directly in the surface 76 by, for example, laser machining or, alternatively, may be formed in a separate band of metal that is affixed to the otherwise smooth-surfaced core 70.

To fashion features 43 in the interior surface 16 of syringe 10, the surface 76 of the core 70 may further include surface features 77 that represent irregularities, indentations, projections, dimples, protuberances, or any other abrupt changes in surface geometry. The resultant shape of features 43 in syringe 10 transferred to the interior surface 16 from surface features 77 may resemble, or otherwise relate to, the appearance of the surface features 77 in core 70. For example, the features 43 may be shallower than the depth of the corresponding surface features 77. The surface features 43, in combination with features 40, collectively define a surface roughness characterizing the interior surface 16.

Surface features 77 may be created on the surface 76 of core 70, for example, as a surface texture by electrical discharge machining (EDM). An exemplary surface texture for creating surface features 77 is a MT-11050 surface texture, as designated by Mold-Tech® Worldwide) having an average feature depth of 0.0045". The invention contemplates that the ribs 74 may be omitted from the core 70 so that features 40 are not formed when the molded syringe 10 is removed from the core 70. In this situation, only surface features 77 will be present on the core 70 and, consequently, only features 43 are formed on interior surface 16. In certain embodiments, the core 70 may be made collapsible so that removal of the syringe 10 from the core 70 does not smooth or otherwise modify the features 43. Changing the level of surface texturing may alter the dimensions of surface features 77, which may therefore decrease or increase the dimensions of features 43 transferred to the interior surface 16.

Figure 9:
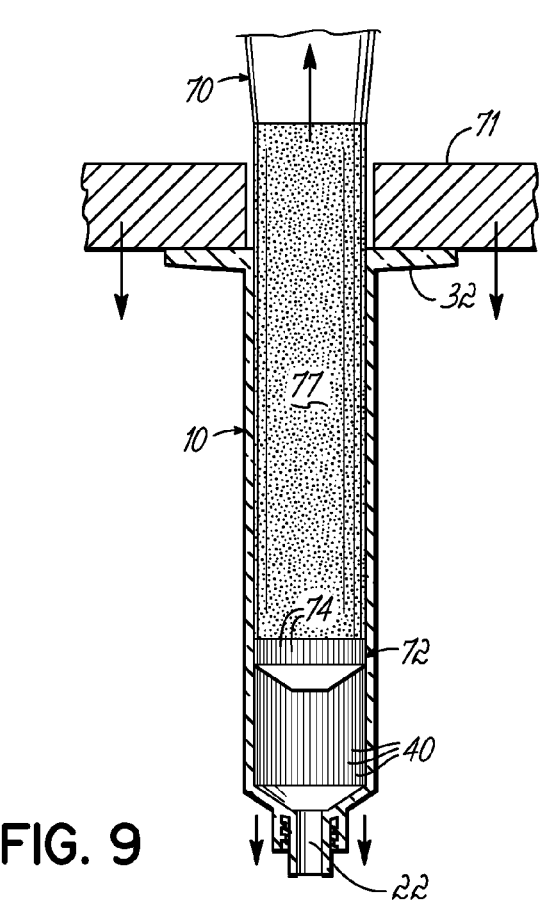
FIG. 9 is a cross-sectional view of the syringe being removed from the core after molding.
Figure 7:
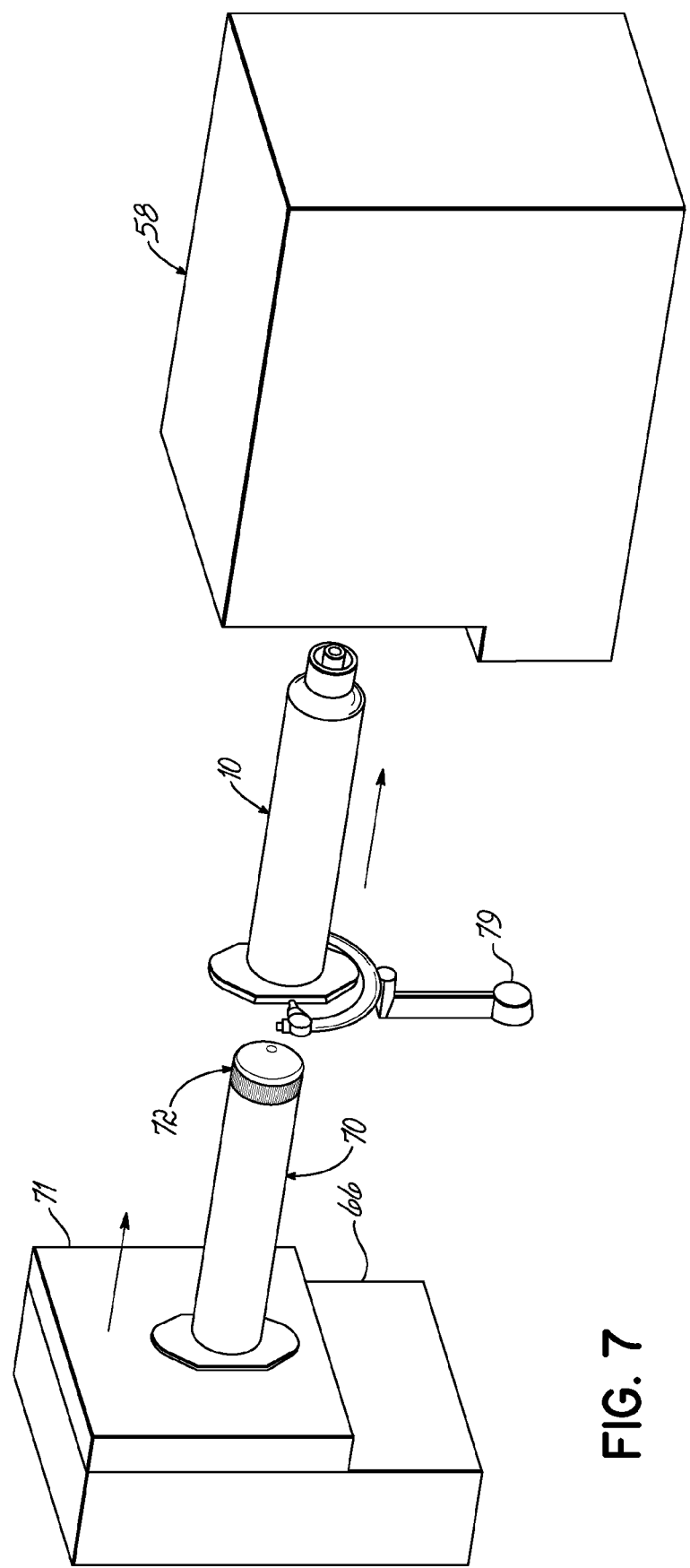
FIG. 7 is an exploded view of the mold of FIG. 5.
Figure 8:
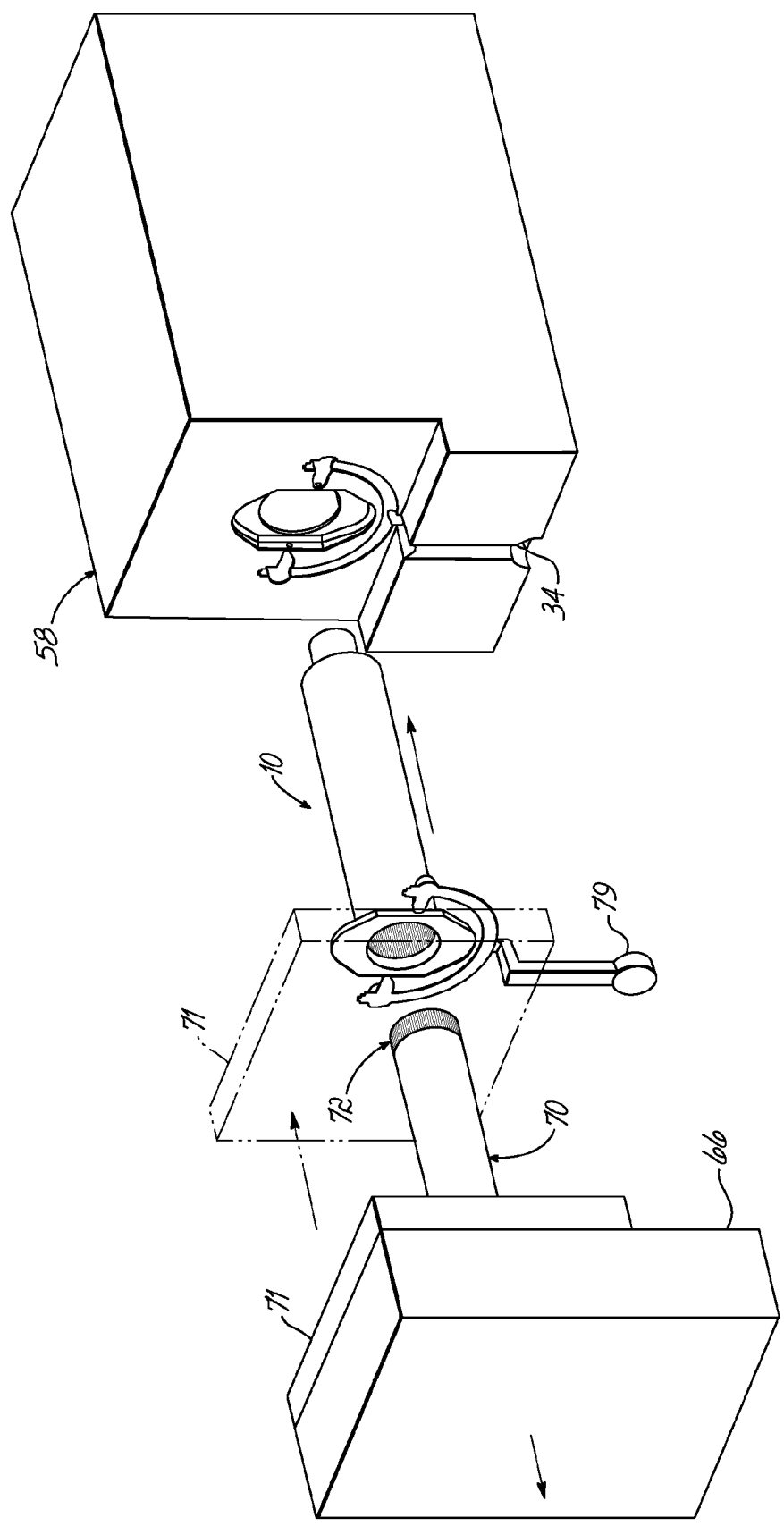
FIG. 8 is another exploded view similar to FIG. 7.

With reference to FIGS. 7-9, after the syringe 10 cools and solidifies, the core 70 is withdrawn from mold 58 and the syringe 10 is removed or separated from the core 70. Removal may be accomplished by contacting the flanges 32a,b with a fixture 71 and moving the fixture 71 so that the syringe 10 slides off the core 70. Close contact is maintained between the tip region 72 and the surface 16 as the syringe 10 is removed from the core 70. The close contact results from the substantially uniform diameter of the core 70 along the length carrying the syringe 10. As the syringe 10 is removed from the core 70, the ribs 74 score the interior surface 16 of the sidewall 14 along its length with features 40 of a complementary or similar shape and dimensions to the ribs 74. As a result, the profile of the ribs 74 in the tip region 72 is transferred as lengthwise-extending and circumferentially spaced features 40 to a coextensive band of the interior surface 16 of the sidewall 14 of the syringe 10. The scored features 40 in the syringe 10 have a substantially uniform draft or depth that is equal or proportional to the depth of the grooves between adjacent ribs 74 of the core 70. The syringe 10 may be warmer than room temperature when removed from the core 70, which assists in forming features 40. Runner 79 attached to the syringe 10 is also removed. The piston 26 (FIG. 1) is inserted into the open rearward end of the barrel 12, either before or after filling the reservoir 28 with fluid 30.

Forming the features 40 in this manner is a relatively clean operation that does not generate debris, that generates insignificant amounts of debris, or that generates fine debris that does not negatively affect the dispensing process (e.g., is fine enough to pass through the smallest-diameter constriction in the fluid flow path). Specifically, the ribs 74 formed features 40 by scoring of the interior surface 16 to displace, or otherwise cut into or gouge, the constituent polymer as the syringe 10 is removed from the core 70. This contrasts with other groove-forming or roughening processes that remove material from the surface 16 to form the features 40 and thereby generate contamination or debris.

In alternative embodiments of the invention, the interior surface 16 of the sidewall 14 may be roughened or textured with any features suitable for increasing the adhesion of the fluid 30 with the sidewall 14. The features in these alternative embodiments may differ in appearance, shape and size from features 40 and/or features 43. For example, the features may be randomly shaped such as resulting from texturing the interior surface 16 with a brush, or other stiff-bristled object, inserted into the barrel 12 and reciprocated and rotated with a sliding action. As another example, the interior surface 16 may be sandblasted or beadblasted. Any debris or contamination resulting form feature generation may be removed by a post-forming cleaning operation. In other embodiments of the invention, the surface 16 may be exposure to a plasma, which may chemically alter and/or physically alter the surface properties depending upon specific characteristics of the plasma treatment. In still other embodiments of the invention, the surface 16 may be roughened by chemically etching using an aqueous etchant.

Figure 10:
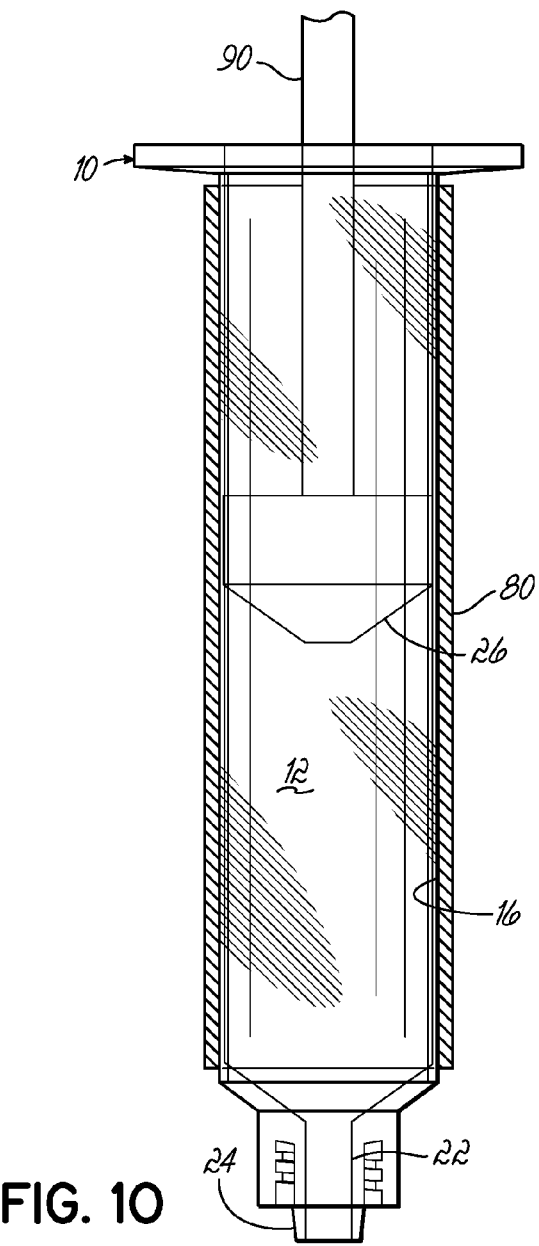
FIG. 10 is a side view of a syringe in partial cross-section in accordance with an alternative embodiment of the invention.

In accordance with an alternative embodiment of the invention and with reference to FIG. 10 in which like reference numerals refer to like features in FIGS. 1 and 2, a jacket or pressure sleeve 80 may be placed about the exterior of the barrel 12 of syringe 10 during the dispensing process. Typically, the sleeve 80 and the sidewall 14 are concentrically arranged and touch at a coextensive cylindrical surfaces defining a support interface therebetween. The use of sleeve 80 reduces the risk of sidewall rupture due to the outward forces generated within the syringe 10 during fluid dispensing when the incompressible fluid 30 is pressurized by applying a force to piston 26 for urging the fluid 30 toward the outlet 22.

A plunger ram 90 of a mechanical actuator, such as a handheld application gun, is inserted into the rearward syringe opening 34 and coupled to the rear end of the piston 26. Forward motion of the actuator advances the plunger ram 90 and piston 26 and, thereby, drives the fluid 30 forward toward the outlet 22 of the syringe 10. Persons of ordinary skill in the art will recognize that air pressure provided in the space above the piston 26 may be used for dispensing the fluid 30 held by the syringe 10, as described above in the context of FIG. 3.

The use of sleeve 80 would be appropriate for those instances in which the sidewall 14 has a thickness that is potentially susceptible to sidewall rupture. Other reinforcing structures and devices are contemplated by the invention. The reduction in the sidewall thickness may follow as a result of introducing features 40 (FIGS. 2, 2A, 2B) and/or features 43 (FIG. 2B).

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method of manufacturing a syringe for dispensing a fluid susceptible to void formation when frozen and thawed before dispensing, comprising:
   forming the syringe about a core inside a mold such that a sidewall of the syringe forms about the core with an inwardly facing surface in contact with the core and a plurality of lengthwise ribs on the surface of the core; and
   separating the syringe from the core such that the ribs score lengthwise grooves in the inwardly-facing surface, the grooves configured to significantly reduce void formation between the inwardly-facing surface and the fluid when the fluid is frozen and thawed.

2. The method of claim 1 wherein forming the syringe further comprises:
   providing surface features on the core and superimposed on at least the ribs that contact with the inwardly-facing surface of the syringe; and
   transferring a replica of the surface features on the core to the inwardly-facing surface.

3. The method of claim 2 wherein providing the features on the core further comprises:
   applying a texture to the core.

4. The method of claim 1 wherein the grooves of the syringe are formed by the removal of the core.

5. The method of claim 1 further comprising:
   Wherein the plurality of ribs are disposed about a tip region of the core.

6. A method of manufacturing a syringe having a fluid reservoir, the method comprising:
   injection molding a syringe about a core having a plurality of lengthwise ribs about a tip region; and
   withdrawing the core from the syringe, wherein the ribs score a plurality of grooves along the fluid reservoir.

7. The method of claim 6 further comprising:
   providing a textured surface to the fluid reservoir prior to withdrawing the core.

8. The method of claim 6 wherein the grooves are formed with one of the following profiles:
   a) double sloped shaped
   b) V-shaped
   c) U-shaped
   d) hemispherical
   e) crescent shaped, and
   f) I-shaped.

* * * * *

UNITED STATES PATENT AND TRADEMARK OFFICE
CERTIFICATE OF CORRECTION

| | | |
|---|---|---|
| PATENT NO. | : 8,241,544 B2 | Page 1 of 1 |
| APPLICATION NO. | : 12/720896 | |
| DATED | : August 14, 2012 | |
| INVENTOR(S) | : Henry Digregorio et al. | |

It is certified that error appears in the above-identified patent and that said Letters Patent is hereby corrected as shown below:

At column 10, claim 5, line 28, change "Wherein" to --wherein--.

Signed and Sealed this
Thirteenth Day of November, 2012

David J. Kappos
*Director of the United States Patent and Trademark Office*